United States Patent [19]

Budnick

[11] 4,116,990
[45] Sep. 26, 1978

[54] CHELATION

[75] Inventor: Edward G. Budnick, Scotch Plains, N.J.

[73] Assignee: Plains Chemical Development Co., Scotch Plains, N.J.

[21] Appl. No.: 688,388

[22] Filed: May 20, 1976

Related U.S. Application Data

[60] Division of Ser. No. 33,513, Apr. 30, 1970, Pat. No. 4,020,091, and a continuation-in-part of Ser. No. 505,471, Oct. 28, 1965, abandoned, and Ser. No. 813,385, Feb. 28, 1969, abandoned, and a continuation-in-part of Ser. No. 485,624, Sep. 7, 1965, Pat. No. 3,471,406, and Ser. No. 482,257, Jun. 24, 1974, Pat. No. 3,471,552.

[51] Int. Cl.$^2$ ............ C07F 1/00; C07F 7/22; C07F 7/24; C07F 9/38
[52] U.S. Cl. ............ 260/429 J; 75/108; 75/118 R; 260/429.2; 260/429.7; 260/429.9; 260/430; 260/435 R; 260/439 R; 423/139
[58] Field of Search ............ 260/502.4 P, 429 R, 260/435, 429.7, 429.9, 439.R, 429.2, 430, 429 J; 423/139; 75/108, 118 R

[56] References Cited

U.S. PATENT DOCUMENTS

| | | | |
|---|---|---|---|
| 2,917,528 | 12/1959 | Ramsey et al. | 260/438.1 |
| 2,964,549 | 12/1960 | Ramsey et al. | 260/439 R X |
| 3,088,799 | 5/1963 | Fetscher | 260/430 X |
| 3,211,521 | 10/1965 | George et al. | 423/139 X |
| 3,214,454 | 10/1965 | Blaser et al. | 260/429.9 |
| 3,234,124 | 2/1966 | Irani | 260/429 R |
| 3,297,578 | 1/1967 | Crutchfield et al. | 260/502.4 P X |
| 3,299,123 | 1/1967 | Fitch | 260/502.4 P |
| 3,320,032 | 5/1967 | Feller | 423/139 X |
| 3,332,986 | 7/1967 | Block et al. | 260/429.9 |
| 3,463,835 | 8/1969 | Budnick | 260/502.4 P |
| 3,471,552 | 10/1969 | Budnick | 260/502.4 P |

Primary Examiner—Helen M. S. Sneed
Attorney, Agent, or Firm—Cushman, Darby & Cushman

[57] ABSTRACT

There is provided a process for chelating non-alkali metal ions comprising contacting said metal ions with a phosphorus chelating compound having a formula selected from the group consisting of:

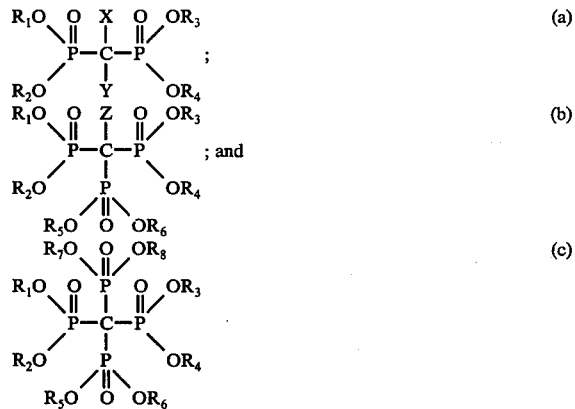

where $R_1$, $R_2$, $R_3$, $R_4$, $R_5$, $R_6$, $R_7$ and $R_8$ are selected from the group consisting of hydrogen, alkali metal and ammonium, X is selected from the group consisting of hydrogen, alkyl, alkenyl, aryl, chloroalkyl, chloroaryl, and halogen of atomic weight 35 to 80, Y is selected from the group consisting of hydroxyl, phenyl and halogen of atomic weight 35 to 80 and Z is selected from the group consisting of hydrogen, phenyl and halogen of atomic weight 35 to 80.

23 Claims, No Drawings

CHELATION

This application is a division of application Ser. No. 33,513 filed Apr. 30, 1970 (U.S. Pat. No. 4,020,091) and is also a continuation-in-part of my copending applications Ser. No. 485,624, filed Sept. 7, 1965, now U.S. Pat. No. 3,471,406 and Ser. No. 482,257, filed 6/24/74, now U.S. Pat. No. 3,491,552, and is also a division of my application Ser. No. 505,471, filed Oct. 28, 1965, now abandoned, and application Ser. No. 813,385, filed Feb. 28, 1969, now abandoned.

This invention relates to novel chelating agents and to novel compositions obtainable therefrom. More particularly, the invention relates to the use of novel polyphosphonic acids and their salts as chelating agents.

It has been proposed in the past to employ methane diphosphonic acid and its alkali metal salts in detergent and wetting compositions (Orthner, German Pat. No. 1,045,373 Dec. 4, 1958). Although methane diphosphonic acid can be used to sequester calcium and other metal ions, there are a number of disadvantages in employing this acid or its alkali metal salts as the sequestering agent in processes such as textile manufacturing and recovery of valuable metals in solution: the sequestering power of methane diphosphonic acid is rather limited and the solubility of the resultant complexes formed by the action of the acid on metal ions can be desirably improved. In any sequestering operation, the amount of ions which can be sequestered by a given amount of the chelating agent is, of course, an important economic consideration. Furthermore, where the reason for using the sequestering agent is to prevent the precipitation of calcium or other metal ions, such as in processes for treating textile materials, the solubility of the complexes formed by the sequestering action is of extreme importance.

It is, therefore, an object of the present invention to provide novel sequestering agents.

It is another object of the invention to provide improved chelating agents with higher solubility and larger chelating capacity.

It is another object of the present invention to provide a novel process for chelating relatively insoluble ions.

It is a further object of the invention to provide a novel process for the recovery of valuable metals from solutions by chelation.

Still other objects and the entire scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

It has now been found that the above objects can be achieved by employing chelating compositions containing polyphosphonic acids and/or alkali metal and ammonium salts thereof having one of the following formulae:

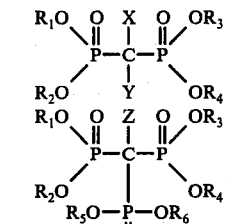

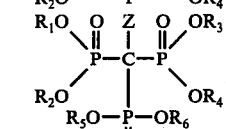

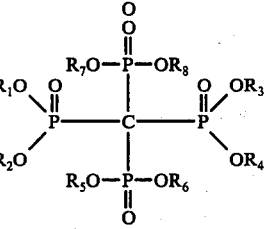

where $R_1$, $R_2$, $R_3$, $R_4$, $R_5$, $R_6$, $R_7$ and $R_8$ are the same or different and are selected from the group consisting of hydrogen, alkali metal (e.g., sodium, potassium, lithium, rubidium or cesium) or ammonium; X is selected from the group consisting of hydrogen, alkyl, alkenyl, chlorine, bromine, aryl (e.g., phenyl or alkylphenyl), chloroalkyl or chloroaryl (e.g., chlorophenyl); Y is selected from the group consisting of hydroxyl, phenyl, chlorine and bromine and Z is selected from the group consisting of phenyl, hydrogen, chlorine and bromine.

Examples of phosphonic acids and their salts useful in the chelating compositions of the present invention are chloromethane diphosphonic acid, dichloromethane diphosphonic acid, bromomethane diphosphonic acid, dibromomethane diphosphonic acid, chloromethane triphosphonic acid, bromomethane triphosphonic acid, methane triphosphonic acid, methane tetraphosphonic acid, hydroxymethane diphosphonic acid, methyl hydroxymethane diphosphonic acid (also called methyl hydroxymethylene diphosphonic acid or 1-methyl-1-hydroxymethane diphosphonic acid), ethyl hydroxymethane diphosphonic acid, butyl hydroxymethane diphosphonic acid, propyl hydroxymethane diphosphonic acid, isopropyl hydroxymethane diphosphonic acid, pentyl hydroxymethane diphosphonic acid, hexyl hydroxymethane diphosphonic acid, heptyl hydroxymethane diphosphonic acid, isoheptyl hydroxymethane diphosphonic acid, octyl hydroxymethane diphosphonic acid, nonyl hydroxymethane diphosphonic acid, decyl hydroxymethane diphosphonic acid, undecyl hydroxymethane diphosphonic acid, dodecyl hydroxymethane diphosphenic acid, tridecyl hydroxymethane diphosphonic acid, tetradecyl hydroxymethane diphosphonic acid, pentadecyl hydroxymethane diphosphonic acid, heptadecyl hydroxymethane diphosphonic acid, octadecyl hydroxymethane diphosphonic acid, nonadecyl hydroxymethane disphosphonic acid, heptadecenyl hydroxymethane diphosphonic acid, vinyl hydroxymethane diphosphonic acid, isopropenyl hydroxymethane diphosphonic acid, chloromethyl hydroxymethane diphosphonic acid, dichloromethyl hydroxymethane diphosphonic acid, trichloromethyl hydroxymethane diphosphonic acid, phenyl hydroxymethane diphosphonic acid, phenyl methane diphosphonic acid, phenyl methane triphosphonic acid, naphthyl hydroxy methane diphosphonic acid, p-chlorophenyl hydroxy methane diphosphonic acid, 2,4.5-trichlorophenyl hydroxy methane diphosphonic acid, 2,4,6-trichlorophenyl hydroxy methane diphosphonic acid, isononyl hydroxy methane diphosphonic acid and the alkali metal and ammonium salts of such phosphonic acids.

Since the phosphonic acids used in the present invention have 4, 6 or 8 acidic hydrogen atoms (Formulae I, II and III respectively) in making the salts one or more of the acidic hydrogen atoms can be replaced by the alkali metal or ammonium ion. Usually all of the acidic hydrogen atoms are replaced in making the salt and unless otherwise indicated when reference is made to a salt in the present specification, all of the acidic hydrogen atoms are replaced. However, it should be understood that this is not an essential part of the present invention and the invention includes the use of the partial as well as the complete salts, e.g., monosodium methane tetraphosphonate, disodium methane tetraphosphonate, trisodium methane tetraphosphonate, tetrasodium methane tetraphosphonate, pentasodium methane tetraphosphonate, hexasodium methane tetraphosphonate, heptasodium methane tetraphosphonate, octasodium methane tetraphosphonate, mono potassium methane tetraphosphonate, tetra potassium methane tetraphosphonate, octa potassium methane tetraphosphonate, mono ammonium methane tetraphosphonate, octa ammonium methane tetraphosphonate, monosodium methane triphosphonate, trisodium triphosphonate, pentasodium methane triphosphonate, hexasodium methane triphosphonate, di potassium methane triphosphonate, tetra potassium methane triphosphonate, hexa potassium methane triphosphonate, mono ammonium methane triphosphonate, hexa ammonium methane triphosphonate, monosodium chloromethane triphosphonate, tetrasodium chloromethane triphosphonate, hexasodium chloromethane triphosphonate, mono potassium chloromethane triphosphonate, tri ammonium chloromethane triphosphonate, hexa ammonium chloromethane triphosphonate, monosodium chloromethane diphosphonate, disodium chloromethane diphosphonate, trisodium chloromethane diphosphonate, tetrasodium chloromethane diphosphonate, mono potassium chloromethane diphosphonate, tetra potassium chloromethane diphosphonate, di ammonium chloromethane diphosphonate, tetra ammonium chloromethane diphosphonate, monosodium dichloromethane diphosphonate, disodium dichloromethane diphosphonate, tetrasodium dichloromethane diphosphonate, tri potassium dichloromethane diphosphonate, tetra potassium dichloromethane diphosphonate, mono ammonium dichloromethane diphosphonate, tetra ammonium dichloromethane diphosphonate, monosodium phenyl methane triphosphonate, trisodium phenyl methane triphosphonate, hexasodium phenyl methane triphosphonate, tetra potassium phenyl methane triphosphonate, hexa potassium phenyl methane triphosphonate, hexa ammonium phenyl methane triphosphonate, tetrasodium hydroxymethane diphosphonate, monosodium methyl hydroxymethane diphosphonate, disodium methyl hydroxymethane diphosphonate, trisodium methyl hydroxymethane diphosphonate, tetrasodium methyl hydroxymethane diphosphonate, potassium methyl hydroxymethane diphosphonate, tetra potassium methyl hydroxymethane diphosphonate, diammonium methyl hydroxymethane diphosphonate, tetra ammonium methyl hydroxymethane diphosphonate, monosodium ethyl hydroxymethane diphosphonate, tetrasodium ethyl hydroxymethane diphosphonate, tri potassium ethyl hydroxymethane diphosphonate, tetra ammonium ethyl hydroxymethane diphosphonate, monosodium propyl hydroxymethane diphosphonate, tetrasodium propyl hydroxymethane diphosphonate, di potassium propyl hydroxymethane diphosphonate, tri ammonium propyl hydroxymethane diphosphonate, disodium isopropyl hydroxymethane diphosphonate, tetra potassium isopropyl hydroxymethane diphosphonate, monosodium chloromethyl hydroxymethane diphosphonate, tetrasodium dichloromethyl hydroxymethane diphosphonate, tetrasodium chloromethyl hydroxymethane diphosphonate, mono potassium chloromethyl hydroxymethane diphosphonate, di potassium chloromethyl hydroxymethane diphosphonate, tetra ammonium chloromethyl hydroxymethane diphosphonate, mono potassium dichloromethyl hydroxymethane diphosphonate, monosodium trichloromethyl hydroxymethane diphosphonate, disodium trichloromethyl hydroxymethane diphosphonate, tetrasodium trichloromethyl hydroxymethane diphosphonate, mono potassium trichloromethyl hydroxymethane diphosphonate, tetra potassium trichloromethyl hydroxymethane diphosphonate, diammonium trichloromethyl hydroxymethane diphosphonate, tetrasodium butyl hydroxymethane diphosphonate, tri potassium butyl hydroxymethane diphosphonate, mono ammonium butyl hydroxymethane diphosphonate, monosodium pentyl hydroxymethane diphosphonate, tetrasodium pentyl hydroxymethane diphosphonate, di potassium pentyl hydroxymethane diphosphonate, monosodium hexyl hydroxymethane diphosphonate, trisodium hexyl hydroxymethane diphosphonate, tetrasodium hexyl hydroxymethane diphosphonate, tetra potassium hexyl hydroxymethane diphosphonate, tetra ammonium hexyl hydroxymethane diphosphonate, tetrasodium heptyl hydroxymethane diphosphonate, disodium heptyl hydroxymethane diphosphonate, mono potassium heptyl hydroxymethane diphosphonate, tri ammonium heptyl hydroxymethane diphosphonate, monosodium octyl hydroxymethane diphosphonate, trisodium octyl hydroxymethane diphosphonate, tetrasodium octyl hydroxymethane diphosphonate, tetra potassium octyl hydroxymethane diphosphonate, tetrasodium nonyl hydroxymethane diphosphonate, tetra ammonium octyl hydroxymethane diphosphonate, tetra potassium nonyl hydroxymethane diphosphonate, tetra ammonium nonyl hydroxymethane diphosphonate, disodium nonyl hydroxymethane diphosphonate, tetrasodium decyl hydroxymethane diphosphonate, di potassium decyl hydroxymethane diphosphonate, mono ammonium decyl hydroxymethane diphosphonate, monosodium isononyl hydroxymethane diphosphonate, tetrasodium isononyl hydroxymethane diphosphonate, trisodium undecyl hydroxymethane diphosphonate, tetra potassium undecyl hydroxymethane diphosphonate, tetrasodium undecyl hydroxymethane diphosphonate, tetra ammonium undecyl hydroxymethane diphosphonate, tetrasodium dodecyl hydroxymethane diphosphonate, tetrasodium tridecyl hydroxymethane diphosphonate, tetra potassium tetradecyl hydroxymethane diphosphonate, monosodium pentadecyl hydroxymethane diphosphonate, trisodium pentadecyl hydroxymethane diphosphonate, tetrasodium pentadecyl hydroxymethane diphosphonate, di potassium pentadecyl hydroxymethane diphosphonate, tetra ammonium pentadecyl hydroxymethane diphosphonate, tetrasodium hexadecyl hydroxymethane diphosphonate, monosodium heptadecyl hydroxymethane diphosphonate, disodium heptadecyl hydroxymethane diphosphonate, trisodium heptadecyl hydroxymethane diphosphonate, tetrasodium heptadecyl hydroxymethane diphosphonate, mono potassium heptadecyl hydroxymethane diphosphonate, tetra potassium heptadecyl hydroxymethane diphosphonate, mono ammonium heptadecyl hydroxymethane diphosphonate, tetrasodium octadecyl hydroxymethane diphosphonate, tetrasodium nonadecyl hydroxymethane diphosphonate, tetra potassium nonadecyl hydroxymethane diphosphonate, tetra ammonium nondecyl hydroxymethane diphosphonate, tetrasodium vinyl hydroxymethane diphosphonate, tetra potassium isopropenyl hydroxymethane diphosphonate, monosodium heptadecenyl hydroxymethane diphosphonate, disodium heptadecenyl hydroxymethane diphosphonate, trisodium heptadecenyl hydroxymethane diphosphonate, tetrasodium heptadecenyl hydroxymethane diphosphonate, mono potassium heptadecenyl hydroxymethane diphosphonate, tetra potassium heptadecenyl hydroxymethane diphosphonate, di ammonium heptadecenyl hydroxymethane diphosphonate, tetra ammonium heptadecenyl hydroxymethane diphosphonate, tetrasodium naphthyl hydroxymethane diphosphonate, monosodium phenyl hydroxymethane diphosphonate, disodium phenyl hydroxymethane diphosphonate, trisodium phenyl hydroxymethane diphosphonate, tetrasodium phenyl hydroxymethane diphosphonate, di potassium phenyl hydroxymethane diphosphonate, tetra potassium phenyl hydroxymethane diphosphonate, tetra ammonium phenyl hydroxymethane diphosphonate, monosodium phenyl methane diphosphonate, disodium phenyl methane diphosphonate, trisodium phenyl methane diphosphonate, tetrasodium phenyl methane diphosphonate, tetra potassium phenyl methane diphosphonate, tetra ammonium phenyl methane diphosphonate, tetrasodium p-chlorophenyl hydroxymethane diphosphonate, tetrasodium 2,4,5-trichlorophenyl hydroxymethane diphosphonate, tetra potassium 2,4,6-trichlorophenyl hydroxymethane diphosphonate.

Alkyltin and aryltin salts (e.g., mono, di or trialkytin salts) can also be made.

Some of the polyphosphonic acids and salts employed in the present invention are old as shown for example, in Blaser U.S. Patent, No. 3,122,417, and Schiefer U.S. Patent, No. 3,149,151. In general the acids and salts can be prepared by the methods shown in Schiefer. Many of the free acids can also be formed by hydrolyzing the corresponding esters such as the esters shown in Schmidt U.S. Patent, No. 2,848,475, for example. Preferably a lower alkyl ester is employed for such a hydrolysis and aqueous hydrochloric acid is used as the hydrolyzing agent as it is illustrated infra. In such case the alkali metal or ammonium salts are formed by dissolving the free acid in aqueous sodium hydroxide or potassium hydroxide or ammonium hydroxide and evaporating to dryness, e.g., by spray drying. Sufficient alkali is employed to neutralize from one up to all the acid groups available on the phosphonic acid. The free methane triphosphonic acid, methane tetraphosphonic acid, chloromethane triphosphonic acid, chloromethane diphosphonic acid and dichloromethane diphosphonic acid and their salts can be prepared in the manner set forth in my copending application Ser. No. 482,257, filed Aug. 24, 1965.

The methane triphosphonic acid, methane tetraphosphonic acid, chloromethane triphosphonic acid and phenyl methane triphosphonic acid and their alkali metal salts are better chelating agents than, for example, methane diphosphonic acid or its alkali metal salts. The alkali metal salts are also more nearly neutral since the tri and tetra phosphonic acids are stronger acids than methane diphosphonic acid.

The novel chelators disclosed herein are better chelating agents for metal ions such as ferric ions than, for example, the well-known conventional sequestering agent ethylene diamine tetraacetic acid.

The hydroxy containing methane diphosphonic acids and alkali metal salts of the present invention, e.g., methyl hydroxymethane diphosphonic acid and their alkali metal salts, have better solubility than the corresponding methane diphosphonic acid or its salts. Additionally, the hydroxy containing compounds have better stability and complex formation properties due to hydrogen bonding available through the hydroxyl hydrogen. All of the above properties of the hydroxy containing compounds are extremely important in processes, such as in the treatment of textile materials, where it is necessary to tie up the calcium and other metal ions in solution and to not to allow these ions to precipitate out so as to discolor the product being treated.

The aryl containing compounds, e.g., phenyl methane diphosphonic acid, phenyl hydroxymethane diphosphonic acid and phenyl methane triphosphonic acid (and their salts), etc., are superior chelating agents for metal extraction, e.g., extraction of gold, silver, vanadium, molybdenum, copper, nickel and iron.

The novel chelating agents disclosed herein are not effective sequesters of mono-valent alkali metals, e.g., lithium, sodium and potassium. They will effectively chelate, however, mono-valent heavy metals such as silver and gold. In general, the chelating agents of the present invention are excellent sequesters of metals belonging to groups Ib, IIa, IIb, IIIa, IIIb, IVa, IVb, Va, Vb, VIa, VIb, VIIa, and VIII in the periodic system of elements. Examples of metals belonging to these groups are copper, silver, gold, magnesium, calcium, barium, zinc, cadmium, mercury, germanium, tin, titanium, zirconium, radium, platinum, palladium, rare earths, e.g. hafnium and cerium, vanadium, chromium, molybdenum, tungsten, uranium, manganese, iron, cobalt and nickel, etc. Thus the novel chelating agents of the present invention are effective chelators of non-alkali metal ions.

Illustrative examples of chelated salts are calcium chloromethane diphosphonate, barium chloromethane diphosphonate, magnesium chloromethane diphosphonate, beryllium chloromethane diphosphonate, zinc chloromethane diphosphonate, cadmium chloromethane diphosphonate, mercury chloromethane diphosphonate, cupric chloromethane diphosphonate, silver chloromethane diphosphonate, auric chloromethane diphosphonate, titanium chloromethane diphosphonate, zirconium chloromethane diphosphonate, stannous chloromethane diphosphonate, stannic chloromethane diphosphonate, chromic chloromethane diphosphonate, tungsten chloromethane diphosphonate, molybdenum chloromethane diphosphonate, manganous chloromethane diphosphonate, ferrous chloromethane diphosphonate, ferric chloromethane diphosphonate, cobaltic chloromethane diphosphonate, nickelous chloromethane diphosphonate, platinum chloromethane diphosphonate, palladium chloromethane diphosphonate, uranium chloromethane diphosphonate, uranyl chloromethane diphosphonate, plumbous chloromethane diphosphonate, hafnium chloromethane diphosphonate, cerium chloromethane diphosphonate, dibutyltin chloromethane diphosphonate, monobutyltin chloromethane diphosphonate, tributyltin chloromethane diphosphonate, dioctyltin chloromethane diphosphonate, diphenyltin chloromethane diphosphonate, calcium bromomethane diphosphonate, ferric bromomethane diphosphonate, barium dibromomethane diphosphonate, cupric dibromomethane diphosphonate, calcium dichloromethane diphosphonate, magnesium dichloromethane diphosphonate, barium dichloromethane diphosphonate, strontium dichloromethane diphosphonate, zinc dichloromethane diphosphonate, beryllium dichloromethane diphosphonate, cadmium dichloromethane diphosphonate, mercury dichloromethane diphosphonate, cupric dichloromethane diphosphonate, silver dichloromethane diphosphonate, auric dichloromethane diphosphonate, titanium dichloromethane diphosphonate, zirconium dichloromethane diphosphonate, stannous dichloromethane diphosphonate, stannic dichloromethane diphosphonate, chromic dichloromethane diphosphonate, tungsten dichloromethane diphosphonate, molybdenum dichloromethane diphosphonate, manganic dichloromethane diphosphonate, ferrous dichloromethane diphosphonate, ferric dichloromethane diphosphonate, cobaltous dichloromethane diphosphonate, nickelic dichloromethane diphosphonate, platinum dichloromethane diphosphonate, palladium dichloromethane diphosphonate, uranium dichloromethane diphosphonate, uranyl dichloromethane diphosphonate, cerium dichloromethane diphosphonate, hafnium dichloromethane diphosphonate, radium dichloromethane diphosphonate, plumbous dichloromethane diphosphonate, dimethyltin dichloromethane diphosphonate, dioctadecyltin dichloromethane diphosphonate, dibutyltin dichloromethane diphosphonate, di (p-tolyl) tin dichloromethane diphosphonate, monooctyltin dichloromethane diphosphonate, trihexyltin dichloromethane diphosphonate, ferric bromomethane triphosphonate, calcium chloromethane triphosphonate, magnesium chloromethane triphosphonate, beryllium chloromethane triphosphonate, strontium chloromethane triphosphonate, barium chloromethane triphosphonate, radium chloromethane triphosphonate, zinc chloromethane triphosphonate, cadmium chloromethane triphosphonate, mercury chloromethane triphosphonate, cupric chloromethane triphosphonate, silver chloromethane triphosphonate, aurous chloromethane triphosphonate, titanic chloromethane triphosphonate, zirconium chloromethane triphosphonate, plumbous chloromethane triphosphonate, stannous chloromethane triphosphonate, stannic chloromethane triphosphonate, chromic chloromethane triphosphonate, tungsten chloromethane triphosphonate, molybdenum chloromethane triphosphonate, manganous chloromethane triphosphonate, ferrous chloromethane triphosphonate, ferric chloromethane triphosphonate, cobaltic chloromethane triphosphonate, nickelous chloromethane triphosphonate, platinum chloromethane triphosphonate, palladium chloromethane triphosphonate, uranium chloromethane triphosphonate, uranyl chloromethane triphosphonate, cerium chloromethane triphosphonate, hafnium chloromethane triphosphonate, dibutyltin chloromethane triphosphonate, dioctyltin chloromethane triphosphonate, amyltin chloromethane triphosphonate, triethyltin chloromethane triphosphonate, di (o-tolyl) tin chloromethane triphosphonate, calcium methane triphosphonate, beryllium methane triphosphonate, magnesium methane triphosphonate, strontium methane triphosphonate, barium methane triphosphonate, radium methane triphosphonate, zinc methane triphosphonate, cadmium methane triphosphonate, mercury methane triphosphonate, cuprous methane triphosphonate, cupric methane triphosphonate, silver methane triphosphonate, auric methane triphosphonate, titanic methane triphosphonate, zirconic methane triphosphonate, plumbous methane triphosphonate, stannous methane triphosphonate, stannic methane triphosphonate, chromous methane triphosphonate, chromic methane triphosphonate, tungsten methane triphosphonate, molybdenum methane triphosphonate, manganous methane triphosphonate, manganic methane triphosphonate, ferrous methane triphosphonate, ferric methane triphosphonate, cobaltous methane triphosphonate, cobaltic methane triphosphonate, nickelous methane triphosphonate, nickelic methane triphosphonate, platinum methane triphosphonate, palladium methane triphosphonate, uranyl methane triphosphonate, hafnium methane triphosphonate, cerium methane triphosphonate, dibutyltin methane triphosphonate, dioctyltin methane triphosphonate, diphenyltin methane triphosphonate, dioctadecyltin methane triphosphonate, dimethyltin methane triphosphonate, di (m-tolyl) tin methane triphosphonate, monobutyltin methane triphosphonate, tributyltin methane triphosphonate, monooctyltin methane triphosphonate, trioctyltin methane triphosphonate, calcium methane tetraphosphonate, magnesium methane tetraphosphonate, barium methane tetraphosphonate, strontium methane tetraphosphonate, radium methane tetraphosphonate, zinc methane tetraphosphonate, cadmium methane tetraphosphonate, mercury methane tetraphosphonate, cuprous methane tetraphosphonate, cupric methane tetraphosphonate, silver methane tetraphosphonate, aurous methane tetraphosphonate, auric methane tetraphosphonate, titanic methane tetraphosphonate, zirconic methane tetraphosphonate, plumbous methane tetraphosphonate, stannous methane tetraphosphonate, stannic methane tetraphosphonate, chromous methane tetraphosphonate, chromic methane tetraphosphonate, beryllium methane tetraphosphonate, tungsten methane tetraphosphonate, molybdenum methane tetraphosphonate, manganous methane tetraphosphonate, manganic methane tetraphosphonate, ferrous methane tetraphosphonate, ferric methane tetraphosphonate, cobaltous methane tetraphosphonate, cobaltic methane tetraphosphonate, nickelous methane tetraphosphonate, nickelic methane tetraphosphonate, platinum methane tetraphosphonate, palladium methane tetraphosphonate, uranium methane tetraphosphonate, uranyl methane tetraphosphonate, hafnium methane tetraphosphonate, cerium methane tetraphosphonate, niobium methane tetraphosphonate, dibutyltin methane tetraphosphonate, dioctyltin methane tetraphosphonate, monobutyltin methane tetraphosphonate, tributyltin methane tetraphosphonate, diphenyltin methane tetraphosphonate, calcium phenyl methane diphosphonate, barium phenyl methane diphosphonate, magnesium phenyl methane diphosphonate, beryllium phenyl methane diphosphonate, zinc phenyl methane diphosphonate, cadmium phenyl methane diphosphonate, mercury phenyl methane diphosphonate, cupric phenyl methane diphosphonate, silver phenyl methane diphosphonate, auric phenyl methane diphosphonate, titanium phenyl methane diphosphonate, zirconium phenyl methane diphosphonate, stannous phenyl methane diphosphonate, stannic phenyl methane diphosphonate, chromic phenyl methane diphosphonate, tungsten phenyl methane diphosphonate, molybdenum phenyl methane diphosphonate, manganous phenyl methane diphosphonate, ferrous phenyl methane diphosphonate, ferric phenyl methane diphosphonate, cobaltic phenyl methane diphosphonate, nickelous phenyl methane diphosphonate, platinum phenyl methane diphosphonate, palladium phenyl methane diphosphonate, uranium phenyl methane diphosphonate, uranyl phenyl methane diphosphonic, plumbous phenyl methane diphosphonate, hafnium phenyl methane diphosphonate, cerium phenyl methane diphosphonate, dibutyltin phenyl methane diphosphonate, monobutyltin phenyl methane diphosphonate, tributyltin phenyl methane diphosphonate, dioctyltin phenyl methane diphosphonate, diphenyltin phenyl methane diphosphonate, calcium phenyl methane triphosphonate, magnesium phenyl methane triphosphonate, beryllium phenyl methane triphosphonate, strontium phenyl methane triphosphonate, barium phenyl methane triphosphonate, radium phenyl methane triphosphonate, zinc phenyl methane triphosphonate, cadmium phenyl methane triphosphonate, mercury phenyl methane triphosphonate, cupric phenyl methane triphosphonate, silver phenyl methane triphosphonate, aurous phenyl methane triphosphonate, titanic phenyl methane triphosphonate, zirconium phenyl methane triphosphonate, plumbous phenyl methane triphosphonate, stannous phenyl methane triphosphonate, stannic phenyl methane triphosphonate, chromic phenyl methane triphosphonate, tungsten phenyl methane triphosphonate, molybdenum phenyl methane triphosphonate, manganous phenyl methane triphosphonate, ferrous phenyl methane triphosphonate, ferric phenyl methane triphosphonate, cobaltic phenyl methane triphosphonate, nickelous phenyl methane triphosphonate, platinum phenyl methane triphosphonate, palladium phenyl methane triphosphonate, uranium phenyl methane triphosphonate, uranyl phenyl methane triphosphonate, cerium phenyl methane triphosphonate, hafnium phenyl methane triphosphonate, dibutyltin phenyl methane triphosphonate, dioctyltin phenyl methane triphosphonate, amyltin phenyl methane triphosphonate, triethyltin phenyl methane triphosphonate, di (o-tolyl) tin phenyl methane triphosphonate, calcium hydroxymethane diphosphonate, barium hydroxymethane diphosphonate, magnesium hydroxymethane diphosphonate, beryllium hydroxymethane diphosphonate, zinc hydroxymethane diphosphonate, cadmium hydroxymethane diphosphonate, mercury hydroxymethane diphosphonate, cupric hydroxymethane diphosphonate, silver hydroxymethane diphosphonate, auric hydroxymethane diphosphonate, titanium hydroxymethane diphosphonate, zirconium hydroxymethane diphosphonate, stannous hydroxymethane diphosphonate, stannic hydroxymethane diphosphonate, chromic hydroxymethane diphosphonate, tungsten hydroxymethane diphosphonate, molybdenum hydroxymethane diphosphonate, manganous hydroxymethane diphosphonate, ferrous hydroxymethane diphosphonate, ferric hydroxymethane diphosphonate, cobaltic hydroxymethane diphosphonate, nickelous hydroxymethane diphosphonate, platinum hydroxymethane diphosphonate, palladium hydroxymethane diphosphonate, uranium hydroxymethane diphosphonate, uranyl hydroxymethane diphosphonate, plumbous hydroxymethane diphosphonate, hafnium hydroxymethane diphosphonate, cerium hydroxymethane diphosphonate, dibutyltin hydroxymethane diphosphonate, calcium methyl hydroxymethane diphosphonate, calcium ethyl hydroxymethane diphosphonate, calcium butyl hydroxymethane diphosphonate, calcium hexyl hydroxymethane diphosphonate, calcium decyl hydroxymethane diphosphonate, calcium pentadecyl hydroxymethane diphosphonate, barium methyl hydroxymethane diphosphonate, barium butyl hydroxymethane diphosphonate, barium hexyl hydroxymethane diphosphonate, magnesium methyl hydroxymethane diphosphonate, magnesium butyl hydroxymethane diphosphonate, magnesium heptyl hydroxymethane diphosphonate, zinc methyl hydroxymethane diphosphonate, beryllium methyl hydroxymethane diphosphonate, cadmium methyl hydroxymethane diphosphonate, mercury methyl hydroxymethane diphosphonate, cupric methyl hydroxymethane diphosphonate, silver methyl hydroxymethane diphosphonate, auric methyl hydroxymethane diphosphonate, titanium methyl hydroxymethane diphosphonate, zirconium methyl hydroxymethane diphosphonate, stannous methyl hydroxymethane diphosphonate, stannic methyl hydroxymethane diphosphonate, chromic methyl hydroxymethane diphosphonate, tungsten methyl hydroxymethane diphosphonate, molybdenum methyl hydroxymethane diphosphonate, manganous methyl hydroxymethane diphosphonate, ferrous methyl hydroxymethane diphosphonate, ferric methyl hydroxymethane diphosphonate, cobaltic methyl hydroxymethane diphosphonate, nickelous methyl hydroxymethane diphosphonate, platinum methyl hydroxymethane diphosphonate, palladium methyl hydroxymethane diphosphonate, uranium methyl hydroxymethane diphosphonate, uranyl methyl hydroxymethane diphosphonate, plumbous methyl hydroxymethane diphosphonate, hafnium methyl hydroxymethane diphosphonate, cerium methyl hydroxymethane diphosphonate, calcium vinyl hydroxymethane diphosphonate, calcium isopropenyl hydroxymethane diphosphonate, barium vinyl hydroxymethane diphosphonate, barium isopropenyl hydroxymethane diphosphonate, magnesium vinyl hydroxymethane diphosphonate, magnesium isopropenyl hydroxymethane diphosphonate, beryllium vinyl hydroxymethane diphosphonate, beryllium isopropenyl hydroxymethane diphosphonate, zinc vinyl hydroxymethane diphosphonate, zinc isopropenyl hydroxymethane diphosphonate, cadmium vinyl hydroxymethane diphosphonate, cadmium isopropenyl hydroxymethane diphosphonate, mercury vinyl hydroxymethane diphosphonate, mercury isopropenyl hydroxymethane diphosphonate, cupric vinyl hydroxymethane diphosphonate, cupric isopropenyl hydroxymethane diphosphonate, silver vinyl hydroxymethane diphosphonate, silver isopropenyl hydroxymethane diphosphonate, auric vinyl hydroxymethane diphosphonate, auric isopropenyl hydroxymethane diphosphonate, titanium vinyl hydroxymethane diphosphonate, titanium isopropenyl hydroxymethane diphosphonate, zirconium vinyl hydroxymethane diphosphonate, zirconium isopropenyl hydroxymethane diphosphonate, stannous vinyl hydroxymethane diphosphonate, stannic vinyl hydroxymethane diphosphonate, chromic vinyl hydroxymethane diphosphonate, tungsten vinyl hydroxymethane diphosphonate, molybdenum vinyl hydroxymethane diphosphonate, manganous vinyl hydroxymethane diphosphonate, ferrous vinyl hydroxymethane diphosphonate, ferric vinyl hydroxymethane diphosphonate, cobaltic vinyl hydroxymehane diphosphonate, nickelous vinyl hydroxymethane diphosphonate, platinum vinyl hydroxymethane diphosphonate, palladium vinyl hydroxymethane diphosphonate, uranium vinyl hydroxymethane diphosphonate, uranyl vinyl hydroxymethane diphosphonate, plumbous vinyl hydroxymethane diphosphonate, hafnium vinyl hydroxymethane diphosphonate, cerium vinyl hydroxymethane diphosphonate, calcium chloromethyl hydroxymethane diphosphonate, calcium dichloromethyl hydroxymethane diphosphonate, calcium trichloromethyl hydroxymethane diphosphonate, calcium chloroethyl hydroxymethane diphosphonate, barium chloromethyl hydroxymethane diphosphonate, magnesium chloromethyl hydroxymethane diphosphonate, beryllium chloromethyl hydroxymethane diphosphonate, zinc chloromethyl hydroxymethane diphosphonate, cadmium chloromethyl hydroxymethane diphosphonate, mercury chloromethyl hydroxymethane diphosphonate, cupric chloromethyl hydroxymethane diphosphonate, silver chloromethyl hydroxymethane diphosphonate, auric chloromethyl hydroxymethane diphosphonate, titanium chloromethyl hydroxymethane diphosphonate, zirconium chloromethyl hydroxymethane diphosphonate, stannous chloromethyl hydroxymethane diphosphonate, stannic chloromethyl hydroxymethane diphosphonate, chromic chloromethyl hydroxymethane diphosphonate, tungsten chloromethyl hydroxymethane diphosphonate, molybdenum chloromethyl hydroxymethane diphosphonate, manganous chloromethyl hydroxymethane diphosphonate, ferrous chloromethyl hydroxymethane diphosphonate, ferric chloromethyl hydroxymethane diphosphonate, cobaltic chloromethyl hydroxymethane diphosphonate, nickelous chloromethyl hydroxymethane diphosphonate, platinum chloromethyl hydroxymethane diphosphonate, palladium chloromethyl hydroxymethane diphosphonate, uranium chloromethyl hydroxymethane diphosphonate, uranyl chloromethyl hydroxymethane diphosphonate, plumbous chloromethyl hydroxymethane diphosphonate, hafnium chloromethyl hydroxymethane diphosphonate, cerium chloromeethyl hydroxymethane diphosphonate, calcium phenyl hydroxymethane diphosphonate, calcium naphthyl hydroxymethane diphosphonate, barium phenyl hydroxymethane diphosphonate, magnesium phenyl hydroxmethane diphosphonate, beryllium phenyl hydroxymethane diphosphonate, zinc phenyl hydroxymethane diphosphonate, cadmium phenyl hydroxymethane diphosphonate, mercury phenyl hydroxymethane diphosphonate, cupric phenyl hydroxymethane diphosphonate, silver phenyl hydroxymethane diphosphonate, aurio phenyl hydroxymethane diphosphonate, titanium phenyl hydroxymethane diphosphonate, zirconium phenyl hydroxymethane diphosphonate, stannous phenyl hydroxymethane diphosphonate, stannic phenyl hydroxymethane diphosphonate, chromic phenyl hydroxymethane diphosphonate, tungsten phenyl hydroxymethane diphosphonate, molybdenum phenyl hydroxymethane diphosphonate, manganous phenyl hydroxymethane diphosphonate, ferrous phenyl hydroxymethane diphosphonate, ferric phenyl hydroxymethane phenyl hydroxymethane diphosphonate, nickelous phenyl hydroxymethane diphosphonate, platinum phenyl hydroxymethane diphosphonate, palladium phenyl hydroxymethane diphosphonate, uranium phenyl hydroxymethane diphosphonate, uranyl phenyl hydroxymethane diphosphonate, plumbous phenyl hydroxymethane diphosphonate, hafnium phenyl hydroxymethane diphosphonate, cerium phenyl hydroxymethane diphosphonate, calcium chlorophenyl hydroxymethane diphosphonate, calcium trichlorophenyl hydroxymethane diphosphonate, barium chlorophenyl hydroxymethane diphosphonate, magnesium chlorophenyl hydroxymethane diphosphonate, beryllium chlorophenyl hydroxymethane diphosphonate, zinc chlorophenyl hydroxymethane diphosphonate, cadmium chlorophenyl hydroxymethane diphosphonate, mercury chlorophenyl hydroxymethane diphosphonate, cupric chlorophenyl hydroxymethane diphosphonate, silver chlorophenyl hydroxymethane diphosphonate, auric chlorophenyl hydroxymethane diphosphonate, titanium chlorophenyl hydroxymethane diphosphonate, zirconium chlorophenyl hydroxymethane diphosphonate, stannous chlorophenyl hydroxymethane diphosphonate, stannic chlorophenyl hydroxymethane diphosphonate, chromic chlorophenyl hydroxymethane diphosphonate, tungsten chlorophenyl hydroxymethane diphosphonate, molybdenum chlorophenyl hydroxymethane diphosphonate, manganous chlorophenyl hydroxymethane diphosphonate, ferrous chlorophenyl hydroxymethane diphosphonate, ferric chlorophenyl hydroxymethane diphosphonate, cobaltic chlorophenyl hydroxymethane diphosphonate, nickelous chlorophenyl hydroxymethane diphosphonate, platinum chlorophenyl hydroxymethane diphosphonate, palladium chlorophenyl hydroxymethane diphosphonate, uranium chlorophenyl hydroxymethane diphosphonate, uranyl chlorophenyl hydroxymethane diphosphonate, plumbous chlorophenyl hydroxymethane diphosphonate, hafnium chlorophenyl hydroxymethane diphosphonate, cerium chlorophenyl hydroxymethane diphosphonate, calcium chloro hydroxymethane diphosphonate, calcium bromo hydroxymethane diphosphonate, barium chloro hydroxymethane diphosphonate, magnesium chloro hydroxymethane disphosphonate, beryllium chloro hydroxymethane diphosphonate, zinc chloro hydroxymethane diphosphonate, cadmium chloro hydroxymethane diphosphonate, mercury chloro hydroxymethane diphosphonate, cupric chloro hydroxymethano diphosphonate, silver chloro hydroxymethane diphosphonate, auric chloro hydroxymethane diphosphonate, titanium chloro hydroxymethane diphosphonate, zirconium chloro hydroxymethane diphosphonate, stannous chloro hydroxymethane diphosphonate, stannic chloro hydroxymethane diphosphonate, chromic chloro hydroxymethane diphosphonate, tungsten chloro hydroxymethane diphosphonate, molybdenum chloro hydroxymethane diphosphonate, manganous chloro hydroxymethane diphosphonate, ferrous chloro hydroxymethane diphosphonate, ferric chloro hydroxymethane diphosphonate, cobaltic chloro hydroxymethane diphosphonate, nickelous chloro hydroxymethane diphosphonate, platinum chloro hydroxymethane diphosphonate, palladium chloro hydroxymethane diphosphonate, uranium chloro hydroxymethane diphosphonate, uranyl chloro hydroxymethane diphosphonate, plumbous chloro hydroxymethane diphosphonate, hafnium chloro hydroxymethane diphosphonate, cerium chloro hydroxymethane diphosphonate, calcium chloromethyl chloromethane diphosphenate, barium chloromethyl chloromethane diphosphonate, magnesium chloromethyl chloromethane diphosphonate, zinc chloromethyl chloromethane diphosphonate, ferric chloromethyl chloromethane diphosphonate, cadmium chloromethyl chloromethane diphosphonate, calcium chlorophenyl chloromethane diphosphonate, barium chlorophenyl chloromethane diphosphonate, zinc chlorophenyl chloromethane diphosphonate, magnesium chlorophenyl chloromethane diphosphonate, ferric chlorophenyl chloromethane diphosphonate, ferrous chlorophenyl chloromethane diphosphonate, calcium phenyl chloromethane diphosphonate, barium phenyl chloromethane diphosphonate, magnesium phenyl chloromethane diphosphonate, calcium methyl chloromethane diphosphonate, barium methyl chloromethane diphosphonate, magnesium methyl chloromethane diphosphonate, calcium diphenylmethane diphosphonate, barium diphenylmethane diphosphonate, magnesium diphenylmethane diphosphonate, calcium vinyl chloromethane diphosphonate, calcium phenyl methyl methane diphosphonate, calcium vinyl phenyl methane diphosphonate, calcium chlorophenyl methyl methane diphosphonate, calcium chlorophenyl phenyl methane diphosphonate.

The chelated salt or the complex formed by the chelating action is useful as a source of the metal chelated. The chelated metal can be recovered from the complex, for example, by driving off the solvent or the liquid medium in which the complex is present. The chelated metal can then be won by flushing the solid complex with a strong acid or base such as nitric soid, hydrochloric acid, potassium hydroxide and sodium hydroxide. Concentrated nitric acid is the preferred reagent for this purpose. The acid will serve to regenerate the polyphosphonic acid chelating agent from the complex at the same time precipitate out the metal, e.g. as cupric nitrate, silver nitrate and uranium chloride, etc. Subsequent purification and recovery steps will follow substantially the known methods.

The complexes found by the chelating agents with the chelated metal ions are themselves useful and valuable products. Thus, for example, the lead salts or chelates of the polyphosphonic acids of the invention are excellent pigments and also are useful as polyvinyl chloride stabilizers. These lead salts or chelates can be prepared, for example, by adding a dilute solution of lead acetate to a polyphosphonic acid such as hydroxy methanediphosphonic acid. Another example is furnished by the dibutyltin derivatives of the polyphosphonic acids which are also polyvinyl chloride stabilizers.

Unless otherwise indicated, all ports and percentages are by weight.

EXAMPLE 1

A 5% aqueous solution of lead acetate containing about 26.6 grams of lead acetate (0.1 mole) was thoroughly mixed with 41.2 grams of hydroxymethyl methanediphosphonic acid. Upon mixing and sitting, the mixture expanded about 50 fold in volume and resulted in a gelatinous solid. This gelatinous solid was found to be an excellent pigment for paints, etc.

About 50 grams of the gelatinous solid containing the lead chelate and made as above were mixed with 450 grams of an oleo resinous clear varnish. This mixture was found to be an excellent material for protectively coating wood, metals, etc. The lead chelate served as the pigment which had very high surface coverage power.

EXAMPLES 2-22

In the following examples, the chelating power of many of the polyphosphonic acids and their salts of the invention was determined as follows:

The chelating agent was first dissolved in kerosene to obtain a 5% solution and this solution was then thoroughly mixed with an aqueous solution containing the metal ions to be chelated in the form of the nitrate. The mixing was sufficient to insure intimate contact between the chelating agent and the metal ions. The pH of the aqueous phase was adjusted by the use of sodium hydroxide. After the thorough mixing, the mixture was allowed to stannd and separate into two phases. Thereafter, the organic phase was physically separated from the aqueous phase. The kerosene solvent was then driven off from the organic phase by heating and the remaining solid burned to obtain the metal chelated in its oxide form. An excess of metal ions was used in the aqueous phase to insure exhaustion of the chelating agent. The metal oxide thus obtained was then weighed and the result was converted to amount of metal so found. The results of these experiments are tabulated below.

TABLE I

| Example No. | Metal Ion Chelated | Chelating Agent | pH | Amount of Metal Chelated mg/gm of Chelator |
|---|---|---|---|---|
| 2 | Fc*** | Phenyl methane diphosphonic acid | 7 | 371 |
| 3 | Fc*** | " | 11 | 252 |
| 4 | Pb** | " | 8 | 241 |
| 5 | Hg** | " | 8 | 199 |
| 6 | Co** | " | 8 | 195 |
| 7 | Zn** | " | 8 | 124 |
| 8 | Cu** | " | 7 | 199 |
| 9 | Fe*** | Phenyl methane triphosphonic acid | 7 | 530 |
| 10 | Fe*** | " | 11 | 359 |
| 11 | Pb** | " | 8 | 344 |
| 12 | Hg** | " | 8 | 284 |
| 13 | Co** | " | 8 | 279 |
| 14 | Zn** | " | 8 | 177 |
| 15 | Cu** | " | 7 | 284 |
| 16 | Fe** | Methane tetraphosphonic acid | 7 | 586 |
| 17 | Fe*** | " | 11 | 398 |
| 18 | Pb** | " | 8 | 381 |
| 19 | Hg** | " | 8 | 314 |
| 20 | Co** | " | 8 | 309 |
| 21 | Zn** | " | 8 | 196 |
| 22 | Cu** | " | 7 | 314 |

Although kerosene was used as the solvent in all of the examples above, other aliphatic or aromatic solvents can be used. Examples of other suitable solvents are naphtha, hexane, octane, decalin, tetralin, petroleum ether, toluene and xylene, etc.

In the above examples, an excess of metal ions was used to determine the chelating capacity of the chelating agents. When the chelating agents are used in actual processes, such as in textile treatment or in the recovery of valuble metals like gold and uranium, a 5 percent excess of the chelating agents is preferably employed to insure the sequestering of all of the metal ions present. It is not necessary to use more than 5 percent excess of the chelators.

In Examples 2 to 15 above, the chelating polyphosphonic acids employed contain a phenyl radical to make the chelator more selectively soluble in the organic phase. When a chelating agent is to be employed in an aqueous system, such as is commonly the case in treating textile materials, then it is preferable to have a hydroxyl group in place of or in addition to the phenyl radical to impart solubility therein.

When the results of Examples 2 and 3 are compared, it is apparent that for a given chelating agent the chelating capacity is increased when the pH is lowered. This rule is generally true for most known chelators.

EXAMPLE 23

About 10 g. of methyl hydroxymethane diphosphonic acid was dissolved in 190 g. of petroleum ether and the solution was then thoroughly mixed with an aqueous solution of ferric nitrate. A large excess of ferric ions was employed. After the thorough mixing, the mixture was allowed to stand and separate into two phases. Thereafter the organic phase was physically separated from the aqueous phase. The petroleum ether solvent was driven off from the organic phase and the solid chelated salt was found to contain iron. However, the amount of iron present in chelated salt was relatively small when compared to the results of Examples 2 and 3. This is probably due to the presence of a hydroxyl group on the central carbon atoms in the chelating diphosphonic acid, which imparted solubility to the chelated salt in the aqueous phase.

EXAMPLES 24–33

Example 23 was repeated except that the chelating agent was replaced as follows:

TABLE II

| Ex. No. | Chelating Agent | Chelated Salt Found |
|---|---|---|
| 24 | Hydroxymethane diphosphonic acid | Ferric hydroxymethane diphosphonate |
| 25 | Hydroxymethane triphosphonic acid | Ferric hydroxymethane triphosphonate |
| 26 | Hydroxy chloromethane diphosphonic acid | Ferric hyroxy chloromethane diphosphonic |
| 27 | Chloromethyl hydroxymethane diphosphonic acid | Ferric chloromethyl hydroxymethane diphosphonate |
| 28 | Methyl hydroxymethane diphosphonic acid | Ferric methyl hydroxymethane diphosphonate |
| 29 | Chloro hydroxymethane diphosphonic acid | Ferric chloro hydroxymethane diphosphonate |
| 30 | Vinyl hydroxymethane diphosphonic acid | Ferric vinyl hydroxymethane diphosphonate |
| 31 | Dichloromethane diphosphonic acid | Ferric dichloromethane diphosphonate |
| 32 | Chloromethane triphosphonic acid | Ferric chloromethane triphosphonate |
| 33 | Dibutyltin methane diphosphonic acid | Ferric dibutyltin methane diphosphonate |

The concentration of the chelating agents which can be suitably employed in the present invention can be varied within a wide range. In general, the concentration of the chelating solution to be used depends on the amount of metal ions to be sequestered and on the solubility of the chelator in the system. I have found that solutions containing between 0.1% to 50% by weight of the chelator are particularly suitable although the chelating agents can be used in an amount of 75% or more of the total solution. The chelated metal complex produced by the reaction of the chelating agent with the metal ion is useful as resin stabilizer. This is particularly true of lead, barium, cadmium, tin and calcium chelate. When used as resin stabilizer the chelated metal complex or metal chelate can be used in an amount of about 0.01% to about 10–15% by weight of the resin. The use of chelated metal complex as resin stabilizer is illustrated by the following example.

EXAMPLE 34

One mole of phenyl hydroxy methane diphosphonic acid was reacted with 2 moles of barium oxide to obtain the barium salt of phenyl hydroxymethane diphosphonic acid. This salt or chelate was then incorporated into a polyvinyl chloride resin formula as follows:

| | |
|---|---|
| PVC resin | 100 grams |
| Dioctyl phthalate | 50 grams |
| Barium salt of phenyl hydroxymethane diphosphonic acid | 2 grams |

The dioctyl phthalate is employed as a plasticizer for the resin.

The above formula was thoroughly mixed and milled at 330° F into a plastic film. The film was then oven aged for 30 minutes at 325° F. After the oven aging the film was essentially colorless and transparent.

When the above resin mixture was repeated but without the use of the barium salt, the resultant film was charred and turned completely black after the same oven aging.

Corresponding cadmium, zinc, strontium, tin and lead salts were also prepared and they were found to possess similar ability to prevent the decomposition and discoloration of chlorinated resins. This was also true of the dioctyltin and dibutyltin chelates of phenyl hydroxymethane diphosphonic acid.

The novel stabilizers of the present invention can be used with halogen containing vinyl and vinylidene resins in which the halogen is attached directly to a carbon atom in the polymer chain. Preferably, the resin is a vinyl halide resin, specifically, a vinyl chloride resin. Usually, the vinyl chloride resin is made from monomers consisting of vinyl chloride alone or a mixture of monomers comprising at least 70% vinyl chloride by weight. When vinyl chloride copolymers are stabilized, preferably the copolymer of vinyl chloride with an ethylenically unsaturated compound copolymerizable therewith contains at least 10% of polymerized vinyl chloride.

As the chlorinated resin there can be employed chlorinated polyethylene having 14 to 75%, e.g., 27% chlorine by weight, polyvinyl chloride, polyvinylidene chloride, polyvinyl bromide, polyvinyl fluoride, copolymers of vinyl chloride with 1 to 90%, preferably 1 to 30%, of a copolymerizable ethylenically unsaturated material such as vinyl acetate, vinyl butyrate, vinyl benzoate, vinylidene chloride, diethyl fumarate, diethyl maleate, other alkyl fumarates and maleates, vinyl propionate, methyl acrylate, 2-ethylhexyl acrylate, butyl acrylate and other alkyl acrylates, methyl methacrylate, ethyl methacrylate, butyl methacrylate and other alkyl methacrylates, methyl alpha chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-1-chloroethylene, acrylonitrile, chloroacrylonitrile, allylidene diacetate and chloroallylidene diacetate. Typical copolymers include vinyl chloride-vinyl acetate (96:4 sold commercially as VYNW), vinyl chloride-vinylacetate (87:13), vinyl chloride-vinyl acetate-maleic anhydride (86:13:1), vinyl chlorine-vinylidene chloride (95:5), vinyl chloride-diethyl fumarate (95:5), vinyl chloride-trichloroethylene (95:5), vinyl chloride-2-ethylhexyl acrylate (80:20).

The stabilizers of the present invention can be incorporated with the resin by admixing in an appropriate mill or mixer or by any of the other well-known methods which provide for uniform distribution throughout the resin compositions. Thus, mixing can be accomplished by milling on rolls at 100°–160° C.

In addition to the novel stabilizers there can also be incorporated with the resin conventional additives such as plasticizers, pigments, fillers, dyes, ultraviolet light absorbing agents, densifying agents and the like.

If a plasticizer is employed, it is used in conventional amount, e.g., 30 to 150 parts per 100 parts of resin. Typical plasticizers are di-2-ethylhexyl phthalate, dibutyl sebacate, dioctyl sebacate, tricresyl phosphate, butyl phthalyl butyl glycolate.

Although several of the uses of the chelating agents of the invention are specifically given and illustrated by examples, it is to be understood that the usefulness of the present chelators is not limited thereto. Other uses of chelating agents are known in the art and a short review of these uses are given by Taylor in his article in the Oct. 20, 1956 issue of Chemistry and Industry at pages 1134–1135.

What is claimed is:

1. A process for chelating non-alkali metal ions comprising contacting said metal ions with a phosphorus chelating compound having a formula selected from the group consisting of:

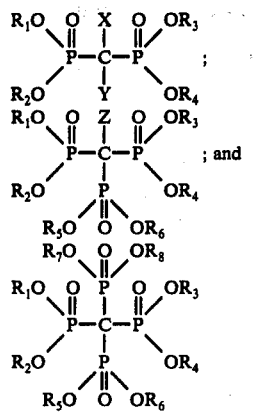

wherein $R_1$, $R_2$, $R_3$, $R_4$, $R_5$, $R_6$, $R_7$ and $R_8$ are selected from the group consisting of hydrogen, alkali metal and ammonium, X is selected from the group consisting of hydrogen, alkenyl, aryl, chloroalkyl, chloroaryl, and halogen of atomic weight 35 to 80, Y is selected from the group consisting of hydroxyl, and halogen of atomic weight 35 to 80 and Z is selected from the group consisting of hydrogen, phenyl and halogen of atomic weight 35 to 80.

2. A process accoding to claim 1 wherein said metal ions are selected from the group consisting of gold ions, silver ions and uranium ions.

3. A process according to claim 1 wherein said metal ions are selected from the group consisting of calcium ions, magnesium ions, iron ions, barium ions, copper ions and lead ions.

4. A process according to claim 1 wherein said phosphorus chelating compound is a member of the group consisting of hydroxymethane diphosphonic acid and its ammonium and alkali metal salts.

5. A process according to claim 1 wherein said phosphorus chelating compound is a member of the group consisting of phenyl hydroxymethane diphosphonic acid, chloromethane diphosphonic acid, dichloromethane diphosphonic acid and their ammonium and alkali metal salts.

6. A process according to claim 1 wherein said phosphorus chelating compound is a member of the group consisting of methane tetraphosphonic acid, methane triphosphonic acid, chloromethane triphosphonic acid, bromomethane triphosphonic acid and ammonium and alkali metal salts of such acids.

7. A process according to claim 1 wherein said phosphorus chelating compound is a member of the group consisting of phenyl methane triphosphonic acid and ammonium and alkali metal salts of such acid.

8. A process for the recovery of non-alkali metal ions from a solution of the same comprising contacting said solution of metal ions with a phosphorus chelating compound having a formula selected from the group consisting of:

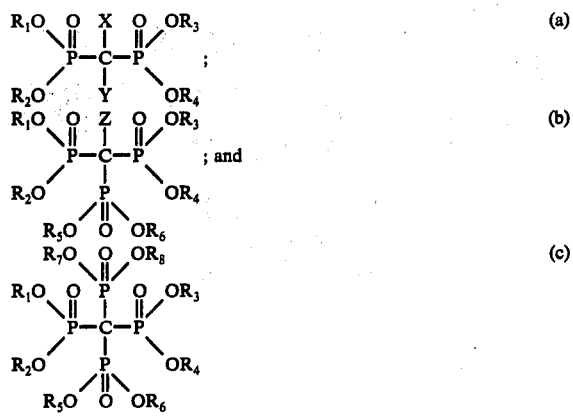

where $R_1$, $R_2$, $R_3$, $R_4$, $R_5$, $R_6$, $R_7$ and $R_8$ are selected from the group consisting of hydrogen, alkali metal and ammonium, X is selected from the group consisting of hydrogen, alkyl, alkenyl, aryl, chloroalkyl, chloroaryl, and halogen of atomic weight 35 to 80, Y is selected from the group consisting of hydroxyl, phenyl and halogen of atomic weight 35 to 80 and Z is selected from the group consisting of hydrogen, phenyl and halogen of atomic weight 35 to 80, thereafter evaporating the solvent to obtain the chelated metal in a complex form and recovering the metal from said metal complex.

9. A process according to claim 8 wherein said non-alkali metal ions are selected from the group consisting of gold ions, silver ions and uranium ions.

10. A process according to claim 8 wherein said phosphorus chelating compound is selected from the group consisting of diphosphonic acid, hydroxymethane triphosphonic acid, methane triphosphonic acid, chloromethane triphosphonic acid, methane tetraphosphonic acid and their alkali metal salts.

11. A process according to claim 8 wherein said phosphorus chelating compound is selected from the group consisting of alkyl hydroxymethane diphosphonic acid, phenyl hydroxymethane diphosphonic acid, phenyl methane triphosphonic acid, and their alkali metal salts.

12. A process according to claim 8 wherein said metal is recovered from said metal complex by washing the metal complex with a concentrated aqueous solution of nitric acid to precipitate the metal nitrate.

13. A process according to claim 5 wherein the phosphorus chelating compound is phenyl hydroxymethane diphosphonic acid or an alkali metal or ammonium salt thereof.

14. A process according to claim 5 wherein the phosphorus chelating compound is chloromethane diphosphonic acid or an alkali metal or ammonium salt thereof.

15. A process according to claim 5 wherein the phosphorus chelating compound is dichloromethane diphosphonic acid or an alkali metal or ammonium salt thereof.

16. A process according to claim 1 wherein the phosphorus chelating compound has formula (b).

17. A process according to claim 1 wherein the phosphorus chelating compound has formula (c).

18. A process according to claim 1 wherein the phosphorus chelating compound has formula (a).

19. A process according to claim 18 wherein X is alkenyl.

20. A process according to claim 18 wherein X is chloroalkyl.

21. A process according to claim 18 wherein X is chloroaryl.

22. A process for chelating non-alkali metal ions comprising contacting said metal ions with a phosphorus chelating compound having the formula:

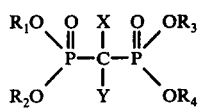

where $R_1$, $R_2$, $R_3$ and $R_4$ are selected from the group consisting of hydrogen, alkali metal and ammonium, X is selected from the group consisting of hydrogen, alkyl, alkenyl, aryl, chloroalkyl, chloroaryl, and halogen of atomic weight 35 to 80 and Y is selected from the group consisting of phenyl and halogen of atomic weight 35 to 80.

23. A process for chelating non-alkali metal ions comprising contacting said metal ions with a phosphorus chelating compound having the formula:

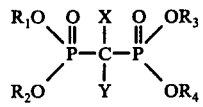

where $R_1$, $R_2$, $R_3$ and $R_4$ are selected from the group consisting of hydrogen, alkali metal and ammonium, X is selected from the group consisting of alkenyl, aryl, chloroalkyl, chloroaryl, and halogen of atomic weight 35 to 80 and Y is selected from the group consisting of hydroxyl, phenyl and halogen of atomic weight 35 to 80.

* * * * *